United States Patent
Booker et al.

(10) Patent No.: US 7,798,020 B2
(45) Date of Patent: Sep. 21, 2010

(54) FAST RESPONSE PROPORTIONAL SAMPLING SYSTEM AND METHOD FOR EXHAUST GAS ANALYSIS

(75) Inventors: David R. Booker, Wantage (GB); Gideon Eden, Ann Arbor, MI (US)

(73) Assignee: Sensors, Inc., Saline, MI (US)

( * ) Notice: Subject to any disclaimer, the term of this patent is extended or adjusted under 35 U.S.C. 154(b) by 406 days.

(21) Appl. No.: 11/883,465

(22) PCT Filed: Jul. 21, 2005

(86) PCT No.: PCT/US2005/025903
§ 371 (c)(1),
(2), (4) Date: Jul. 31, 2007

(87) PCT Pub. No.: WO2006/012433
PCT Pub. Date: Feb. 2, 2006

(65) Prior Publication Data
US 2008/0190168 A1 Aug. 14, 2008

Related U.S. Application Data

(60) Provisional application No. 60/589,750, filed on Jul. 21, 2004.

(51) Int. Cl.
G01N 1/22 (2006.01)
G01N 1/38 (2006.01)
(52) U.S. Cl. .................................... 73/863.03
(58) Field of Classification Search ................ 73/28.01, 73/23.31, 23.33, 863.02–863.03, 863.31, 73/863.33; 436/179
See application file for complete search history.

(56) References Cited

U.S. PATENT DOCUMENTS 2,644,934 A * 7/1953 Grant, Jr ............... 73/863.33 X
4,106,910 A * 8/1978 Saunders .................... 436/179

(Continued)

FOREIGN PATENT DOCUMENTS

EP         1333270 A1 *    8/2003

(Continued)

OTHER PUBLICATIONS

International Search Report of the International Searching Authority from Patent Cooperation Treaty (PCT) Application No. PCT/US05/25903 from which the present application claims priority, mailed Jul. 2006, made available on PATENTSCOPE Search Service Nov. 2006.

(Continued)

*Primary Examiner*—Thomas P Noland
(74) *Attorney, Agent, or Firm*—Van Dyke, Gardner, Linn & Burkhart, LLP

(57) ABSTRACT

A method and apparatus for proportional sampling of particulate material present in the exhaust gas emitted from an engine, in order to measure the mass of particulate material present in the exhaust gas, utilizes a mixing chamber (18) for mixing a portion of the exhaust gas with a dilution gas. A flow control (20) controls the flow rate of the portion of the exhaust gas as a function of exhaust gas flow by activating individual ones of a parallel array of solenoid valves (30), each defining a flow restriction (34).

28 Claims, 7 Drawing Sheets

U.S. PATENT DOCUMENTS

| | | | |
|---|---|---|---|
| 4,402,910 A * | 9/1983 | Smith et al. | 422/83 |
| 5,976,889 A * | 11/1999 | Hirai et al. | 436/179 X |
| 6,134,942 A * | 10/2000 | Pasquereau et al. | 73/23.31 |
| 6,200,819 B1 * | 3/2001 | Harvey et al. | 436/179 |
| 6,513,397 B2 * | 2/2003 | Pasquereau et al. | 73/863.33 |
| 2003/0079555 A1 * | 5/2003 | Dickson et al. | 73/863.02 |
| 2003/0136177 A1 * | 7/2003 | Hendren et al. | 73/23.31 |
| 2004/0118223 A1 * | 6/2004 | Dickson et al. | 73/863.03 X |
| 2005/0016298 A1 * | 1/2005 | Hill | 73/863.03 |
| 2005/0217351 A1 * | 10/2005 | Kreck et al. | 73/863.02 X |

FOREIGN PATENT DOCUMENTS

| | | | |
|---|---|---|---|
| JP | 10104134 A * | 4/1998 | |
| JP | 10111222 A * | 4/1998 | |
| WO | WO 02070116 A1 * | 9/2002 | |
| WO | WO 02071030 A1 * | 9/2002 | |

OTHER PUBLICATIONS

International Preliminary Report on Patentability completed Mar. 14, 2007, made available on PATENTSCOPE Search Service Nov. 2007.

* cited by examiner

| Solenoid Bit Control | 2 | 4 | 8 | 16 | 32 | 64 | 128 | 256 | 512 | 1054 |
|---|---|---|---|---|---|---|---|---|---|---|
| Target Flow (LPM) | 0.06 | 0.11 | 0.23 | 0.46 | 0.91 | 1.82 | 3.64 | 7.29 | 14.57 | 30.00 |
| Orifice Diameter (mm) | 0.08 | 0.11 | 0.16 | 0.23 | 0.32 | 0.45 | 0.64 | 0.90 | 1.28 | 1.83 |

FIG. 7

FAST RESPONSE PROPORTIONAL SAMPLING SYSTEM AND METHOD FOR EXHAUST GAS ANALYSIS

CROSS REFERENCE TO RELATED APPLICATIONS

This application is a filing under 35 U.S.C. §371 of International Application No. PCT/US05/25903, filed on Jul. 21, 2005, which claims priority from U.S. provisional patent application Ser. No. 60/589,750, filed on Jul. 21, 2004, the disclosures of which are hereby incorporated herein by reference in their entirety.

BACKGROUND OF THE INVENTION

The present invention pertains to a fluid dilution sampling apparatus for either proportional sampling or fixed dilution sampling of a fluid. The invention is useful with any source, but has particular application to exhaust analysis. While the invention is illustrated for engine exhaust emission analysis and, in particular, to measuring the mass of particulate matter in the engine exhaust, it may also be used for exhaust analysis for boilers, industrial stacks, and the like.

When a gasoline-or diesel-engined vehicle is driven, carbon particles and condensed high-boiling-point hydrocarbons are emitted from the tailpipe, generating particulate matter (PM) after being diluted and cooled in ambient air. In order to measure PM emissions using simulated driving conditions in the laboratory, a dilution tunnel is traditionally used. Previously, in order to measure PM, only a steady-state test cycle was required and the dilution systems were mainly total dilution types, dubbed full-flow dilution tunnels. These tunnels were very large and could occupy most of the test cell space.

Recently, a new transient engine test has been under consideration as a more realistic simulation of PM measurement than the steady-state test cycle. At the same time, the technique known as partial exhaust dilution sampling has been considered as the basis of measuring particulates from this new transient engine test. Partial exhaust dilution systems work by sampling part of the engine exhaust gas-flow, keeping a constant split ratio (the ratio of exhaust total flow to sampled flow). This is carried out by mixing the sample gas with dilution air inside a small dilution chamber and then the diluted exhaust gas passes through filters where the particulate material is deposited.

For proportional sampling, the control of the dilution air requires fast response to control inputs. There are two major factors that affect delay in flow control during a transient cycle: firstly, the time delay of the exhaust-gas flow rate measurement itself and the delay for the sample to reach the sampling point from the engine (exhaust measuring point); the second factor is the delay in the flow control of the dilution tunnel. The first factor can be corrected by using a predictive control method. Overcoming the problems posed by the second factor, i.e., speeding up the response time of the dilution tunnel flow control, has been addressed by the following:

A first approach replaced the traditional vortex blower rotation control method (used on full flow dilution systems) with a flow control method that used a piezo-valve to control the flow rate of compressed air used for dilution. This approach came from a design for a hot-wire type mass-flow controller that uses a piezo control valve. Such devices are in common use, although their accuracy and response speed are not satisfactory for use in this application.

A second approach combines a piezo-valve with a venturi flowmeter. In addition to these components, by using a critical flow orifice (CFO) with the piezo-valve, the response time can be reduced to 0.2 second in open-loop control of the piezo-valve. This technique is still too slow.

SUMMARY OF THE INVENTION

The present invention provides a fast dilution sampling control system which can be used as either a proportional sampling system or a fixed dilution system and method for exhaust analysis that overcomes the difficulties set forth above.

A dilution apparatus for sampling of a source gas emitted from a source includes a flowmeter, a mixing chamber, a first flow control and a processing unit. The flowmeter is adapted to measuring a parameter that is indicative of the flow rate of the source gas. The mixing chamber is adapted to mixing a portion of the source gas with a dilution gas, thereby generating a diluted sample. The first flow control is adapted to at least partially controlling the flow rate of the portion of the source gas. The first flow control includes a first parallel array of solenoid valves, each defining a flow restriction. The processing unit is responsive to an output of the flowmeter. The processing unit controls the sampling ratio of the source gas by activating the combination of the solenoid valves of the first parallel array as a function of the flow rate of the source gas.

The dilution apparatus may further include a second flow control. The second flow control is adapted to at least partially controlling the flow rate of the diluted sample. The second flow control includes a second parallel array of solenoid valves, each defining a flow restriction. The processing unit controls the flow rate of the diluted sample from the mixing chamber at least in part by activating a combination of the solenoid valves of the second parallel array as a function of the flow rate of the source gas. The processing unit may control the flow rate of the sample from the mixing chamber at a generally constant flow rate.

The flow restriction may be a flow orifice, a critical flow orifice and/or a needle valve. At least some of the solenoid valves have different flow restrictions than others of the solenoid valves.

The apparatus may include one or more particulate analyzers for analyzing the diluted sample for particulate mass. The particulate analyzer may include a particulate filter, wherein the diluted sample is conveyed through the particulate filter for trapping of the particulate matter present in the diluted sample. The particulate filter may be weighed for the determination of the mass of the particulate matter trapped in the particulate filter.

The apparatus may include a calibration flowmeter to balance the airflow of the first control with the flow rate of the diluted sample produced with the second flow control.

The apparatus may be adapted for use with an exhaust producing apparatus, such as an engine exhaust. The processing unit may control the flow rate of the dilution apparatus to provide proportional sampling or fixed dilution sampling.

A method for diluting a source gas emitted from the source, according to an aspect of the invention, includes sampling the source gas to provide a portion of the source gas and measuring a parameter indicative of the flow rate of the source gas. A dilution gas is provided at a flow rate. The portion of the source gas is mixed with the dilution gas, thereby generating a diluted sample. The flow rate of the portion of the source gas is at least partially controlled with the first parallel array of solenoid valves, each defining a flow restriction. The sampling ratio of the source gas is controlled by activating a combination of the solenoid valves of the first array as a function of the flow rate of the source gas.

The method may further include controlling the flow rate of the diluted sample with a second parallel array of solenoid valves, each defining a flow restriction. The flow rate of the diluted sample may be controlled by activating a combination of the solenoid valves of the second parallel array as a function of the flow rate of the source gas. The diluted sample flow rate may be controlled at a generally constant flow rate.

At least one particulate analyzer may be provided and a portion of the diluted sample provided to the particulate analyzer to analyze the mass of the particulate matter of the diluted sample. The mass of the particulate matter contents present in the source gas may be determined from the mass of the particulate matter of the diluted sample, the flow rate of the diluted sample and the flow rate of the source gas. The at least one particulate analyzer may measure light-scattering and/or electrical charge. The at least one particulate analyzer may measure the mass of particulate matter trapped at a substrate placed in a stream of the diluted sample. The substrate may oscillate at a frequency related to the mass of the particulate matter collected from the diluted sample or may oscillate at an amplitude related to the mass of the particulate matter and the diluted sample.

The method may be used to measure particulate matter in an exhaust, such as an engine exhaust. The sampling may be proportional sampling or fixed dilution sampling.

These and other objects, advantages and features of this invention will become apparent upon review of the following specification in conjunction with the drawings.

BRIEF DESCRIPTION OF THE DRAWINGS

FIG. 7 is a table illustrating dimensions of critical orifice(s) for each "bit" control.

DESCRIPTION OF THE PREFERRED EMBODIMENT

Figure 1:
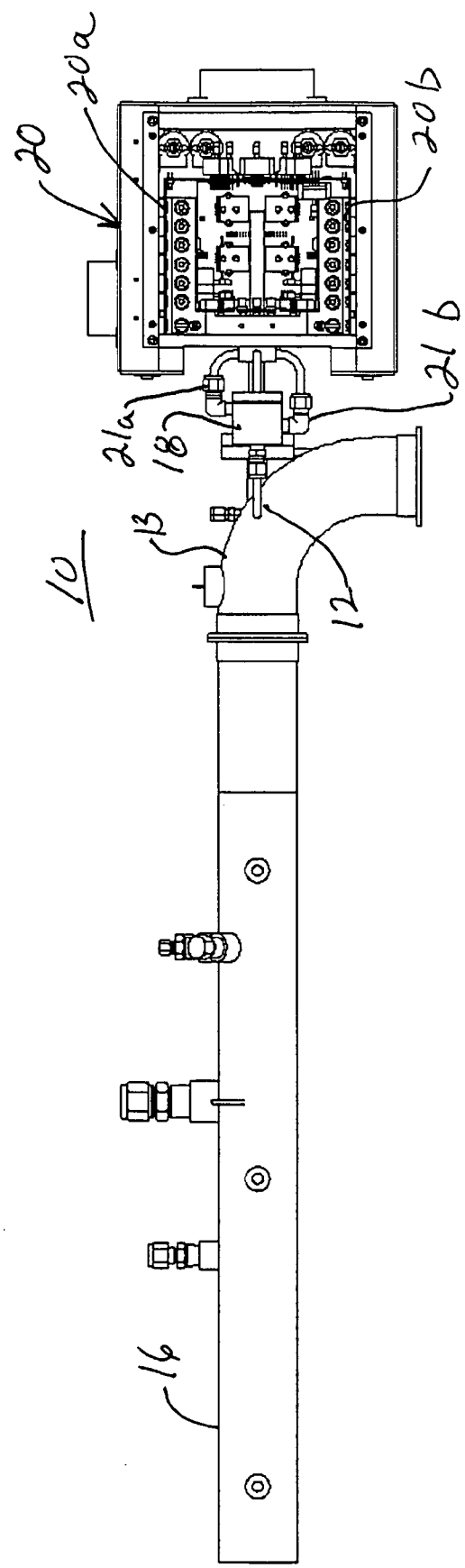
FIG. 1 is a side elevation of an engine exhaust analyzer, according to the invention.
Figure 2:
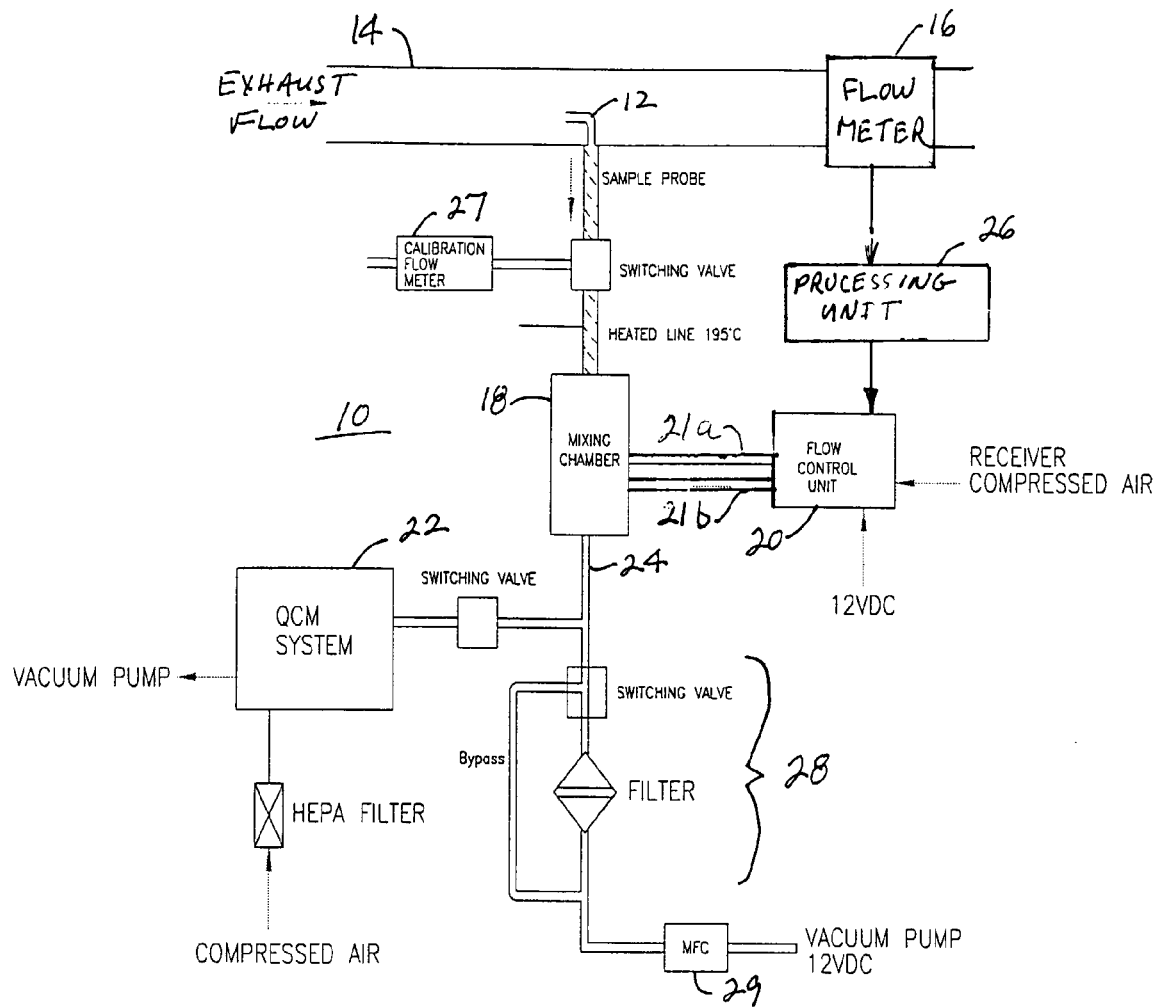
FIG. 2 is a block diagram of the exhaust analyzer in FIG. 1.

Referring now specifically to the drawings, and the illustrative embodiments depicted therein, an engine exhaust analyzer 10 for measuring the mass of particulate matter in the exhaust of an engine includes a sample probe 12 for sampling exhaust gas from a tailpipe 14 and a flowmeter 16 for measuring the flow rate of the exhaust gas (FIGS. 1 and 2). Analyzer 10 further includes a mixing chamber 18 that mixes exhaust gas from sample probe 12 with a dilution gas from a flow control unit 20. A particulate analyzer 22 for analyzing particulate matter, such as for particulate mass discharged over a given period of time, retrieves at least a portion of the diluted sample from discharge 24 of mixing chamber 18 at a generally constant flow rate. A second particulate analyzer 28 may also be provided to analyze particulate matter from discharge 24. It should be understood that only one particulate analyzer or more than two particulate analyzers can be used.

In the illustrated embodiment, flowmeter 16 is an EFM exhaust flowmeter that is commercially available from Sensors, Inc. of Ann Arbor, Mich. Analyzer 10 may include a fitting, such as an elbow 13, that allows mixing chamber 18 to be positioned close to probe 12. This may eliminate the need for a heated line between probe 12 and chamber 18.

Figure 3:
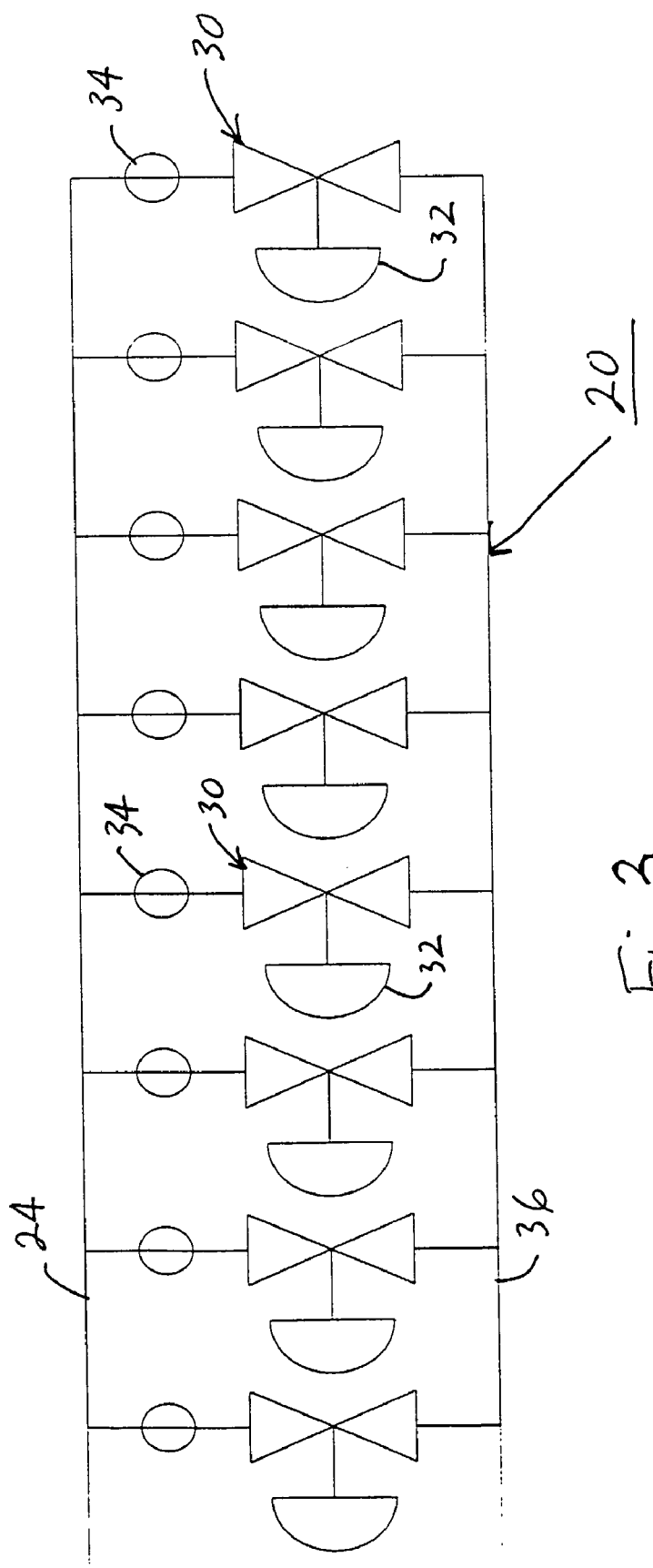
FIG. 3 is a schematic diagram illustrating operation of a flow control unit, according to the invention.
Figure 4:
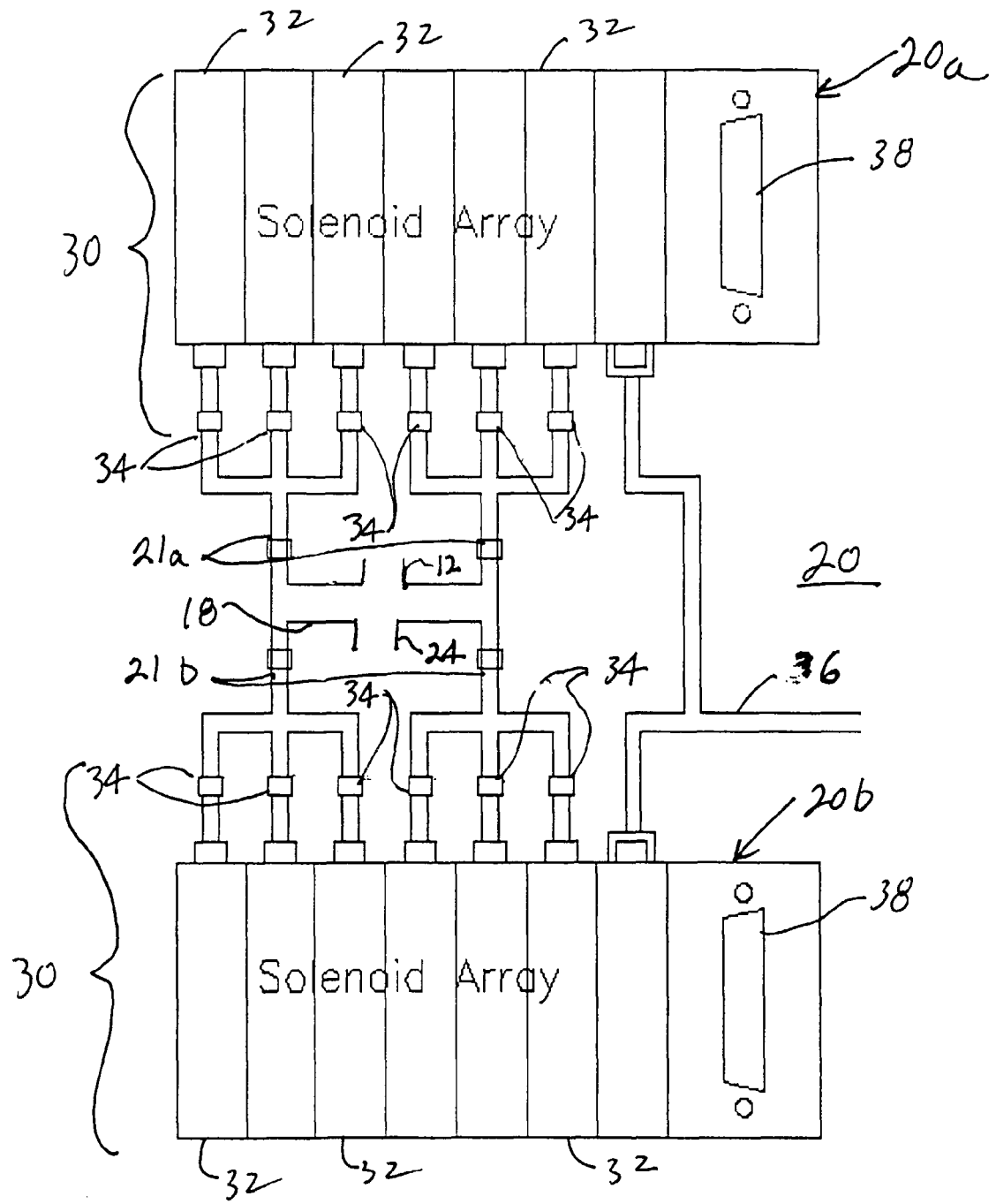
FIG. 4 is a block diagram of the flow control unit in FIG. 3.
Figure 5:
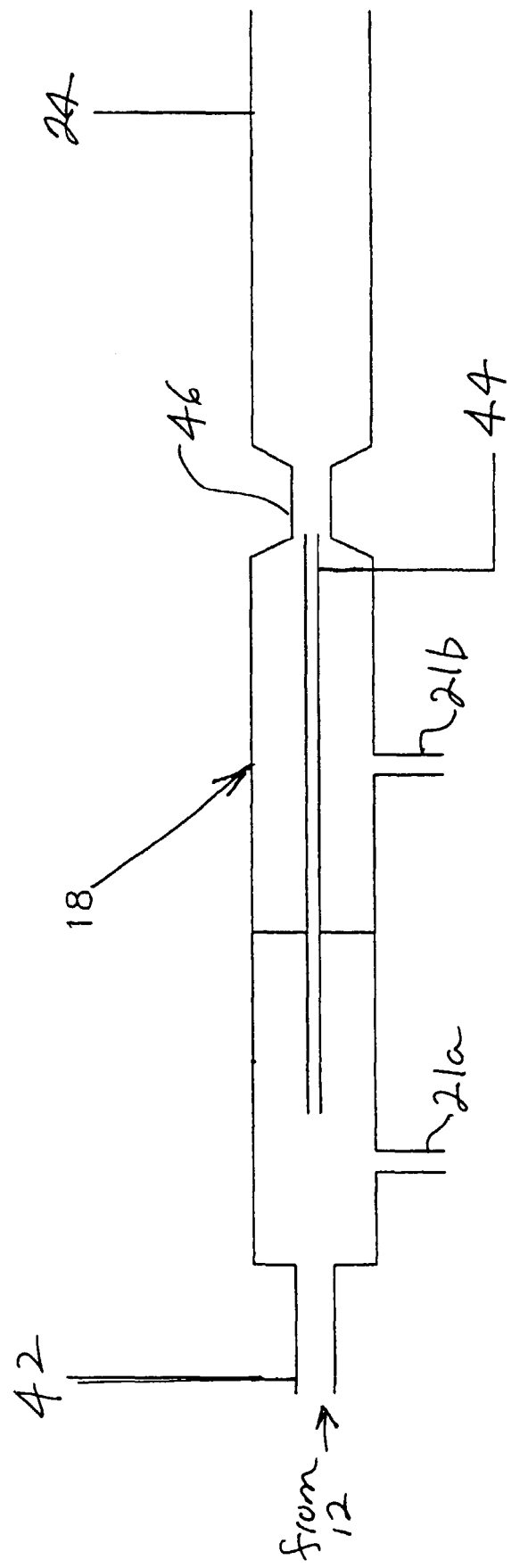
FIG. 5 is a schematic diagram of a mixing chamber, illustrating operation thereof.
Figure 6:
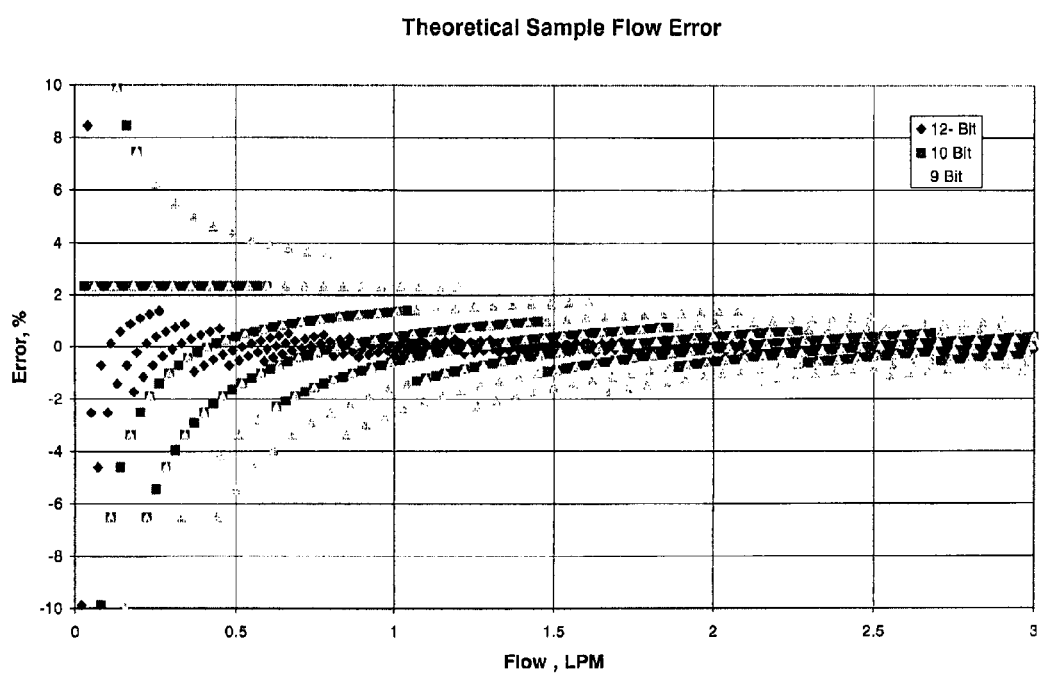
FIG. 6 is a chart illustrating theoretical sample flow air as a function of flow rate.

A processing unit 26 retrieves the flow rate of the exhaust gas from flowmeter 16 and controls the flow rate of dilution gas, such as air, from flow control unit 20. Flow control unit 20 is made up of at least one parallel array of solenoid valves 30 (FIGS. 3 and 4). Each of the solenoid valves 30 defines a flow restriction. Each of the solenoid valves has a solenoid actuator 32 and an associated flow orifice 34. Each flow orifice is made up of a flow restriction that may operate as a critical flow orifice (critical flow orifice) or may be a non-critical flow orifice or a needle valve. At least some of the flow orifices are different from other flow orifices and, in the illustrative embodiment, each flow orifice is different from the other flow orifices 34. When a particular actuator 32 is actuated by processing unit 26, dilution gas from a compressed air manifold 36 is supplied through one or more of the flow orifices 34 in parallel, thereby producing a controlled flow of dilution gas. In the illustrated embodiment, flow control unit 20 is made up of a first dilution flow control 20a and a second dilution flow control 20b. Outlets of flow orifices of first dilution flow control 20a are collected at first diluted sample output 21a. Outlets of second dilution flow control 20b are collected at second diluted sample output 21b. Outputs 21a, 21b are supplied to mixing chamber 18. Each flow control unit 20a, 20b includes one or more electrical connectors 38 for electrical interconnection with a control unit of processing unit 26.

The dilution flow is controlled by flow control unit 20 using a pair of multi-bit parallel solenoid arrays. Each array is made up of a plurality of solenoids 30, each associated with a critical flow orifice 34 (or critical adjustable needle valve) to provide precise and repeatable flow characteristics. This system may be operated at 10-20 Hz, thereby providing approximately 50 ms to 100 ms adjustment of the dilution flow. Slower or faster control is also possible. A positive feedback loop with exhaust flowmeter 16 is used to meet proportional sampling requirements. As an alternative to flowmeter 16, a flow input signal that is proportional to exhaust flow, such as a fuel flow signal, a combustion air flow signal, or the like, may be used.

On the assumption that the minimum dilution ratio required to meet the filter face temperature within specification was 10:1, and the filter flow rate is 30 liters per minute (LPM), the following error analysis, based on the largest error source namely the sample flow, illustrates the system theoretical performance. For performance at a turn-down ratio of 10:1, the sample flow (3/10 LPM=0.130 LPM) can be achieved within acceptable error limits. As can be seen below in Table 1 for a 12-bit system, this flow can be set within approximately 1% absolute. Similarly, for a 9 and 10-bit system, the errors are approximately 10% and approximately 3%, respectively.

A portion of the bits are included in first dilution flow control 20a and a portion is included in a second dilution flow control 20b. First dilution flow control 20a is controlled to provide the correct dilution ration to obtain a certain proportion of the exhaust flow. This is accomplished by a venturi 40 in mixing chamber 40. Venturi 40, in the illustrative embodiment, includes a laminar flow capillary 42, a secondary transport capillary 44 and a flow restriction 46. As processing unit 26 determines a change in exhaust gas flow rate, it selects particular solenoids 30 to activate in the first flow control 20a.

This changes the flow of dilution air at 21*a*, which causes a change in vacuum at venturi 40. This results in a change in the sample flow rate from probe 12, corresponding to the change in exhaust flow from the engine, to maintain a particular dilution ratio. Second dilution flow control 20*b* provides a make up flow of dilution gas in order to maintain total sample flow rate from mixing chamber 18 at a near constant flow rate. As processing unit 26 determines a change in exhaust gas flow rate, it determines an additional amount of dilution air required to bring the flow rate at discharge 24 to a particular level.

Operation of apparatus 10 includes obtaining a particulate sample over a given sample period and measuring mass of the sample. Because flow control 20 is able to maintain a generally constant sampling, or dilution, ratio at a generally constant flow rate, it is not necessary to consider in the calculations the amount of dilution air used. Mixing chamber 18, in the illustrated embodiment, includes a flowmeter (not shown), such as an internal flowmeter, for direct measurement of sample flow rate. The flowmeter associated with mixing chamber 18 provides an input to processing unit 26 representative of actual sample flow. Processing unit 26 uses this sample flow signal to monitor system performance, not to operate flow control 20.

The dimensions of the critical orifice(s) used for each "bit" control are illustrated in FIG. 7 for a range of flow rates (10-bit system illustrated). Other values may be used. For a 12-bit system with a filter flow rate of 30 LPM, the smallest orifice diameter would be 28 um (70 cc/min). In applications where orifice diameter is small, the flow orifice may be replaced with a critical flow needle valve, for example.

To compensate for any error in machining orifice diameters and to provide a more exact calculated flow rate, the system may be calibrated for flow over the complete range of operation, such as by using a calibration flowmeter 27. Under such scheme, the flow characteristics for each orifice are measured and used to generate a "look-up" table correlating the actual flow rate to a binary array (bit control number). This calibration is then checked by measuring the sample flow rate over the appropriate range using the Filter Mass Flowmeter as a reference flowmeter.

In the illustrative embodiment, particulate analyzer 22 may utilize known particulate analysis techniques. Examples of known particulate analyzers utilize various techniques, such as light-scattering principles electrical charge generated by the particulate matters as well as a particulate filter for trapping the particulate matter present in the exhaust gas. In the illustrative embodiment, particulate analyzer 28 is a gravimetric meter and utilizes a mass flow controller 29 to draw a controlled amount of flow needed for the particulate analyzer. However, other known particulate analyzers may be used.

Thus, it is seen that the present invention provides a very fast dilution flow control system that is capable of exceptional accuracy, as required for the application. An orifice flow balancing system may be used to auto-calibrate or balance the dilution airflow rate and filter flow.

Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows:

1. A dilution apparatus for sampling of a source gas emitted from a source, said apparatus comprising:

a flowmeter, said flowmeter adapted to measuring a parameter indicative of flow rate of the source gas;

a mixing chamber, said mixing chamber adapted to mixing a portion of the source gas with a dilution gas, thereby generating a diluted sample;

first flow control, said first flow control adapted to at least partially controlling the flow rate of the portion of the source gas, said first flow control comprising a first parallel array of solenoid valves, each defining a flow restriction, wherein at least one of said flow restrictions comprises an adjustable critical flow restriction;

a processing unit responsive to an output of said flowmeter, said processing unit controlling the sampling ratio of the source gas by activating a combination of said solenoid valves of said first parallel array as a function of the flow rate of the source gas.

2. The dilution apparatus as claimed in claim 1 including a second flow control, said second flow control adapted to at least partially controlling the flow rate of the diluted sample, said second flow control comprising a second parallel array of solenoid valves, each defining another flow restriction, wherein at least one of said another flow restrictions comprises an adjustable critical flow restriction, wherein said processing unit controls the flow rate of the diluted sample from said mixing chamber at least in part by activating a combination of said solenoid valves of said second parallel array as a function of the flow rate of the source gas.

3. The dilution apparatus as claimed in claim 2, wherein said processing unit controls the flow rate of the diluted sample from said mixing chamber at a generally constant flow rate.

4. The dilution apparatus as claimed in claim 1, wherein each said flow restriction comprises a flow orifice.

5. The dilution apparatus as claimed in claim 1, wherein each said flow restriction comprises a critical flow orifice.

6. The dilution apparatus as claimed in claim 1, wherein said adjustable critical flow restriction comprises a needle valve.

7. The dilution apparatus as claimed in claim 1, wherein at least some of said solenoid valves have different flow restrictions than other of said solenoid valves.

8. The dilution apparatus as claimed in claim 1, wherein said mixing chamber is adapted to mixing a portion of the sample gas with the dilution gas comprising ambient air.

9. The dilution apparatus in claim 1 further includes at least one particulate analyzer, said at least one particulate analyzer adapted to analyzing the diluted sample for particulate mass.

10. The dilution apparatus as claimed in claim 9, wherein said at least one particulate analyzer includes a particulate filter, wherein the diluted sample is conveyed through said particulate filter for trapping the particulate matter present in the diluted sample.

11. The dilution apparatus as claimed in claim 10, wherein said particulate filter is adapted to be weighed for the determination of the mass of the particulate matter trapped in said particulate filter.

12. The dilution apparatus as claimed in claim 1 further including a calibration flowmeter, said calibration flowmeter adapted to balancing the airflow of said first flow control with the flow rate of the diluted sample produced with said second flow control.

13. The dilution apparatus as claimed in claim 1 adapted for use with an exhaust—producing apparatus, wherein the source gas is an exhaust gas of said exhaust producing apparatus.

14. The dilution apparatus as claimed in claim 13, wherein the exhaust producing apparatus comprises an engine and the exhaust gas comprises engine exhaust.

15. The dilution apparatus as claimed in claim 1, wherein said processing unit controls the flow rate of the dilution apparatus to provide one chosen from proportional sampling control and fixed dilution sampling control.

16. Method for diluting a source gas emitted from a source, said method comprising:

sampling the source gas to provide a portion of the source gas;

measuring a parameter indicative of the flow rate of the source gas;

providing a dilution gas at a flow rate;

mixing the portion of the source gas with the dilution gas, thereby generating a diluted sample;

at least partially controlling the flow rate of the portion of the source gas with a first parallel array of solenoid valves, each defining a flow restriction, wherein at least one of said flow restrictions comprises an adjustable critical flow restriction;

controlling the sampling ratio of the source gas by activating a combination of said solenoid valves of said first parallel array as a function of the flow rate of the source gas.

17. The method as claimed in claim 16 further including controlling the flow rate of the diluted sample with a second parallel array of solenoid valves, each defining another flow restriction, wherein at least one of said another flow restrictions comprises an adjustable critical flow restriction, including controlling the flow rate of the diluted sample by activating a combination of said solenoid valves of said second parallel array as a function of the flow rate of the source gas.

18. The method as claimed in claim 17 including controlling the diluted sample flow rate at a generally constant flow rate.

19. The method as claimed in claim 16 including providing at least one particulate analyzer, supplying at least a portion of the diluted sample to said particulate analyzer and analyzing the mass of the particulate matter of the diluted sample by said particulate analyzer.

20. The method as claimed in claim 19 including computing the mass of the particulate matter contents present in the source gas from the mass of the particulate matter of said diluted sample, the flow rate of the diluted sample and the flow rate of the source gas.

21. The method as claimed in claim 19, wherein said at least one particulate analyzer measures light-scattering.

22. The method as claimed in claim 19, wherein said at least one particulate analyzer measures electrical charge.

23. The method as claimed in claim 22, wherein said at least one particulate analyzer measures mass of particulate matter trapped at a substrate placed in a stream of the diluted sample.

24. The method as claimed in claim 23, wherein said substrate oscillates at a frequency related to the mass of the particulate matter collected from the diluted sample.

25. The method as claimed in claim 23, wherein said substrate oscillates at an amplitude related to the mass of the particulate matter in said diluted sample.

26. The method as claimed in claim 16 used to measure particulate matter in an exhaust.

27. The method as claimed in claim 26 used to measure particulate matter in an engine exhaust.

28. The method as claimed in claim 16, wherein said sampling comprises one chosen from proportional sampling and fixed dilution sampling.

* * * * *